United States Patent
Orihara et al.

(10) Patent No.: US 11,639,918 B2
(45) Date of Patent: May 2, 2023

(54) SOIL, MOISTURE INDICATOR, WATER DETECTION UNIT USED IN SOIL, MOISTURE INDICATOR, BODY CASE, MANUFACTURING METHOD FOR WATER DETECTION UNIT, AND MANUFACTURING METHOD FOR SOIL MOISTURE INDICATOR

(71) Applicant: CABINOTIER CO., LTD., Tokyo (JP)

(72) Inventors: Ryo Orihara, Tokyo (JP); Fumiya Asa, Tokyo (JP)

(73) Assignee: CABINOTIER CO., LTD., Tokyo (JP)

( * ) Notice: Subject to any disclaimer, the term of this patent is extended or adjusted under 35 U.S.C. 154(b) by 313 days.

(21) Appl. No.: 16/644,758

(22) PCT Filed: Sep. 10, 2018

(86) PCT No.: PCT/JP2018/033512
§ 371 (c)(1),
(2) Date: Mar. 5, 2020

(87) PCT Pub. No.: WO2019/050037
PCT Pub. Date: Mar. 14, 2019

(65) Prior Publication Data
US 2021/0190743 A1    Jun. 24, 2021

(30) Foreign Application Priority Data
Sep. 8, 2017   (JP) .............................. JP2017-173476

(51) Int. Cl.
*G01N 31/22* (2006.01)
*G01N 21/78* (2006.01)
(Continued)

(52) U.S. Cl.
CPC ........... *G01N 31/222* (2013.01); *G01N 21/78* (2013.01); *G01N 21/81* (2013.01); *G01N 33/246* (2013.01); *G01N 2021/7766* (2013.01)

(58) Field of Classification Search
CPC ........... G01N 2021/7766; G01N 21/78; G01N 21/81; G01N 31/222
(Continued)

(56) References Cited

U.S. PATENT DOCUMENTS

| | | | | |
|---|---|---|---|---|
| 3,951,098 A | * | 4/1976 | Meyers | G01N 21/29 73/73 |
| 4,382,380 A | * | 5/1983 | Martin | G01N 33/246 73/73 |
| 8,997,682 B1 | * | 4/2015 | Ashcroft | G01N 21/29 116/200 |
| 2016/0123867 A1 | * | 5/2016 | Orihara | G01N 33/246 73/73 |

FOREIGN PATENT DOCUMENTS

JP    9-15237    1/1997
JP    3070450    8/2000
(Continued)

OTHER PUBLICATIONS

PCT/JP2018/033512, International Search Report (ISR) and Written Opinion (WO), dated Jan. 8, 2019, 6 pages—English, 7 pages—Japanese.
(Continued)

*Primary Examiner* — Maureen Wallenhorst
(74) *Attorney, Agent, or Firm* — Andrew F. Young; Nolte Lackenbach Siegel

(57) ABSTRACT

A soil moisture indicator contains a water-absorbing material and a color-changing part. A body part is formed and hollow by a material through which water does not pass, and has a water-absorbing opening proximate one end and a transpiration opening positioned near the other end. A dis-
(Continued)

play part is connected to the other end of the body part and allows an inner hollow portion to be viewed. An upper-end part that constitutes the end portion of the display part can be removed from and connected to the display part at the end portion on the opposite side to the end portion connected to the body. There is a change in color tone indication between a water-absorbed state and a dry state.

3 Claims, 25 Drawing Sheets

(51) Int. Cl.
*G01N 21/81* (2006.01)
*G01N 33/24* (2006.01)
*G01N 21/77* (2006.01)

(58) Field of Classification Search
USPC ......... 422/400, 401, 402, 405, 412, 420, 69; 436/164, 165, 169
See application file for complete search history.

(56) References Cited

FOREIGN PATENT DOCUMENTS

| | | |
|---|---|---|
| JP | 3136622 | 11/2007 |
| JP | 4382380 | 12/2009 |
| JP | 2014-238381 | 12/2014 |
| JP | 2015-152341 | 8/2015 |

OTHER PUBLICATIONS

Microfilm of the specification and drawings annexed to the request of Japanese Utility Model Application No. 57496/1988 (Laid-open No. 162652/1989) (Fujimoto, Yasuyoshi) Nov. 13, 1989, claims, specification, pag 6, Fig. 1,2, 4 (Family: none), 4 pages—English, 14 pages—Japanese.

Microfilm of the specification and drawings annexed to the request of Japanese Utility Model Application No. 117728/1976 (Laid-open No. 36381/1978) (Tatsumoto, Jiro, Kobayashi, Hitoshi) Mar. 30, 1978, claims fig. 1, 2 (Family: none), 3 pages—English, 7 pages—Japanese.

* cited by examiner

SOIL, MOISTURE INDICATOR, WATER DETECTION UNIT USED IN SOIL, MOISTURE INDICATOR, BODY CASE, MANUFACTURING METHOD FOR WATER DETECTION UNIT, AND MANUFACTURING METHOD FOR SOIL MOISTURE INDICATOR

CROSS REFERENCE TO RELATED APPLICATIONS

This application relates to and claims priority as a § 371 national phase, from PCT/JP2018/033512 filed Sep. 10, 2018, the entire contents of which are incorporated herein by reference, which in turn claims priority from JP 2017-173476 filed Sep. 8, 2017.

TECHNICAL FIELD

The present invention relates to a water detection unit and a main body case (housing) to be applied to a soil moisture indicator that indicates a watering timing for maintaining a suitable water content for growing plants in soil and a manufacturing method for the water detection unit.

BACKGROUND

An indicator is proposed to display a water moisture (content) to maintain the suitable water content for growing plants in soil. For example, an apparatus to measure humidity of soil based on a change of the electric resistance of the soil humidity detector (e.g., refer to Patent Document 1) and an indicator for the different color corresponding to the water content in soil by installing a porous layer, of which transparency is different between the liquid absorbed state and the liquid unabsorbed state, so as to contact with the water absorbing material capable of absorbing water (e.g., refer to Patent Document 2) have been proposed. In addition to the above, a measurement instrument called pF meter is commercially available, in which the number (value) instructed therein must be read out as well as illustrated in Patent Document 1 and the price thereof is quite high, so that such an instrument cannot be readily used without circumstances.

The wet level of the soil can be denoted by the value called "pF value". Such a pF value is the pressure unit representing the strength to gravitate the soil water by the capillary force. Given the soil includes water well, the pF value is smaller and indicates that the plant root can absorb water readily. In contrast, given the soil turns dry, the pF value becomes high, so that the plant needs stronger force to soak up water. In the field, the normal pF value is 1.5 to 2.7 (effective growing water); and when less than that, water is too much; and when more than that, water is less.

The pF value that does not provide the plant with a stress is in the range of pF 1.7 to 2.3, varying with the variety of plants for growing. Accordingly, the indicator must display the state in which the soil is too dry when the pF value is exceeding the suitable value corresponds to the plant. However, according to the plant electronic soil humidity measurement apparatus of Patent Document 1, an electric device is used to measure the water content, so that an electric battery (battery) is mandatory, and when the battery is out of power, such a measurement becomes unavailable and the display becomes out of order. In addition, unless the digital display is read out, the water content cannot be available, so that it is too hard to know the dryness of the soil and to decide whether watering is needed or not. In addition, according to the indicator of Patent Document, no battery is needed, but it is too hard to adjust the water content (pF value), at which the color change takes place, to a suitable value for each kind of a cultivating plant.

Accordingly, the present inventors visualized the soil dryness reaching a predetermined and a desirable level and created a soil moisture indicator that can inform the fact to a user (Patent Document 3). Such a soil moisture indicator comprises: a main body housing; a water-absorbing material housed in the main body housing; and a color changing unit changing at the position of the color on the display of the main body housing in accordance with the water absorbed state and the dry state.

RELATED PRIOR ART DOCUMENTS

Patent Document

Patent Document 1: JP Utility Model Patent Registration No. 3070450 B1
Patent Document 2: JP Utility Model Patent Registration No. 3136622 B1
Patent Document 3: JP Patent 5692826 B1

ASPECTS AND SUMMARY OF THE PRESENT INVENTION

Objects to be Solved

With respect to the soil moisture indicator disclosed in Patent Document 3, it is desirable that the water-absorbing material and the color changeable unit housed in the main body housing can be changeable. For example, it may be expected to change such a water-absorbing material with the water-absorbing material and the color change unit that can help to make a decision as to the best pF value corresponding to each plant when the water-absorbing material is deteriorated.

The purpose of the present invention is to provide a soil moisture indicator, a water detection unit used for the soil moisture indicator and a main body case (housing), and further manufacturing methods for the water detection unit and the soil moisture indicator.

Means for Solving the Problem

According to the aspect of the present invention to solve the above problem, a water detection unit that is applied to a soil moisture indicator, of which the outer appearance changes corresponding to the water content in the soil, comprises:
a water-absorbing material that is installed to have a rod-like shape; and
a color changeable unit that is installed around the outer circumference of the water-absorbing material and varies a color tone thereof in accordance with a water absorbing state and a dry state.

According to such a structure, the water detection unit having the color changeable unit around the rod-shaped water-absorbing material and exchangeable can be provided.

With respect to the water detection unit used for the soil moisture indicator of the present invention, the water-absorbing material may comprise an unwoven cloth and a super absorbent polymer adhered to the unwoven cloth. Accordingly, the rod-shape can be formed out of the unwoven cloth and the water absorbability due to the density of the unwoven cloth can be easily adjusted. In addition, the superabsorbent polymer can increase the water absorbability with the unwoven cloth.

With respect to the water detection unit used for the soil moisture indicator of the present invention, the water-absorbing material may comprise a preservative and a binder. Such a preservative can prevent corrosion of the water detection unit. In addition, the binder can maintain the adhesion state of the preservative and the superabsorbent polymer to the water-absorbing material and improve to keep the shape of the water-absorbing material.

With respect to the water detection unit used for the soil moisture indicator of the present invention, the water-absorbing material includes a chemical fiber and outer circumference of the water-absorbing material made of the chemical fiber, which can be harder than the inner circumference of the water-absorbing material made of the chemical fiber. Accordingly, the rod-shaped water detection unit can be provided due to the water absorbability and formability of the chemical fiber.

According to the aspect of the present invention to solve the above problem, a water detection unit that is applied to a soil moisture indicator, of which the outer appearance changes corresponding to the water content in the soil, comprises: a cylinder housing; a water-absorbing material that the cylinder housing houses thereinside; a color change unit that is installed around the outer circumference of the cylinder housing and varies a color tone thereof in accordance with a water absorbing state and a dry state.

According to such a structure, the water detection unit that has a rod-shape and is exchangeable can be provided, wherein the water-absorbing material and the color change unit is being supported as the cylinder housing functions to keep the shape thereof. The water-absorbing material is not housed in the cylinder of the cylinder housing, so that the water-absorbing material won't swell even when not used for a long time and accordingly, can be easily mounted on the indicator.

With respect to the water detection unit used for the soil moisture indicator of the present invention, the tip portion from the one end of the cylinder housing to the predetermined position has a reduced diameter, so that the water-absorbing material can be housed in the other end portion rather than the tip portion. Accordingly, the water-absorbing material can be held without falling off from the one end of the cylinder housing. In addition, the tip portion has the reduced diameter, the color changeable unit can be easily inserted from the tip portion and in addition, easily inserted into the main body housing.

With respect to the water detection unit used for the soil moisture indicator of the present invention, the color changeable unit can be mounted slidably to the cylinder housing. Accordingly, the cylinder housing alone can be pulled out easily while leaving the water-absorbing material and the color changeable unit in the main housing.

When the soil moisture indicator has a hollow made of the material through which water does not passes; a water absorption opening near by the one end thereof in the longitudinal direction; and a main body housing having the display installed to the other end, the length of the water-absorbing material can be longer than the length between water absorption opening and the other end. Accordingly, when the water detection unit is inserted into the main housing, the water-absorbing material is set up at the location of the water absorption opening so as to project from the other end of the main body housing.

The present invention provides a main body housing capable of storing the above water detection unit comprises: a main body unit having a hollow structure made of a water blocking material and a water absorbing opening in a proximity of one end thereof in a longitudinal direction; and a display that is connected to the other end of the main body unit and at least a part of such a display is made of a clear material that allows to recognize visually recognizing a hollow space inside thereof, wherein the inner diameter of the display is larger than the inner diameter of the main body unit. According to such a structure, the water-absorbing material can be set up in the main body unit and the color changeable unit can be set up in the display when the water detection unit is inserted into the main body unit.

According to the main body housing of the present invention, the inner diameter of the main body unit can be larger than the outer diameter of the cylinder housing and smaller than the inner diameter of the color changeable unit, and the inner diameter of the display can be larger than the outer diameter of the color changeable unit. As a result, the water detection unit can be inserted into the main body housing together with the whole cylinder housing, and then after, only the cylinder housing can be pulled out from the main body housing while leaving the water-absorbing material in the main body unit and the display and the color changeable unit at the position of the display.

According to the main body housing, the tip of the cylinder housing can project from the one end and the end portion of the water-absorbing material can project from the other end when the water detection unit is stored. Accordingly, the cylinder housing projected from the one end is pulled in the state at which the other end of the water-absorbing material projected from the other end after the water detection unit is housed in the main body housing is being held, so that only the cylinder housing projected from the one end can be pulled out while leaving the water-absorbing material and the color changeable unit in the main body housing.

According to the aspect of the present invention to solve the above problem, a manufacturing method for a water detection unit that is applied to a soil moisture indicator, of which outer appearance changes corresponding to the water content in the soil, comprises steps of: inserting a water-absorbing material into a cylinder from one end of a cylinder housing; storing the water-absorbing material in the other side than a tip portion between the one end of the cylinder housing and a predetermined position; reducing a diameter of the tip portion of the cylinder housing; and mounting a color changeable unit, which varies a color tone thereof in accordance with a water absorbing (wet) state and a dry state, on the outer circumference of the cylinder housing. According to such an aspect, the water detection unit that has a rod-shaped and is exchangeable can be manufactured, wherein the water-absorbing material and the color changeable unit is being supported as the cylinder housing functions to keep the shape thereof.

According to the manufacturing method for the water detection unit of the present invention, the step of inserting the water-absorbing material can include the step of inserting the water-absorbing material into the cylinder housing while twisting the water-absorbing material. According to such a step, the density of the water-absorbing material can be adjusted in accordance with the twisting level. According to the manufacturing method for the water detection unit of the present invention, the step of mounting the color changeable unit can include the step of shaping the color changeable unit to provide the cylinder-shape and inserting the color changeable unit from the one end of the cylinder housing. According to such an aspect, the cylinder-shape color changeable unit can be easily mounted on the exterior of the cylinder housing.

Effects of the Present Invention

According to the aspect of the present invention, the water-absorbing material and the color changeable unit can be exchanged easily.

DETAILED DESCRIPTION OF THE PREFERRED EMBODIMENTS

The inventor sets forth the aspects Embodiments of the present invention based on the following FIGs. In addition, the same member has the same sign in the followings and an explanation of the member once explained is arbitrarily skipped as to such a member.

Figure 1A:
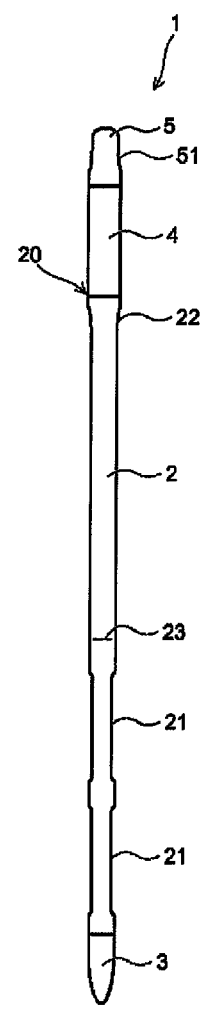
FIG. 1A is a front view illustrating an example of the soil moisture indicator.
Figure 1B:
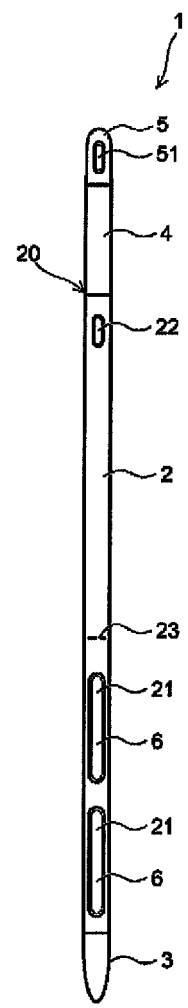
FIG. 1B is a side view illustrating an example of the soil moisture indicator.
Figure 2A:
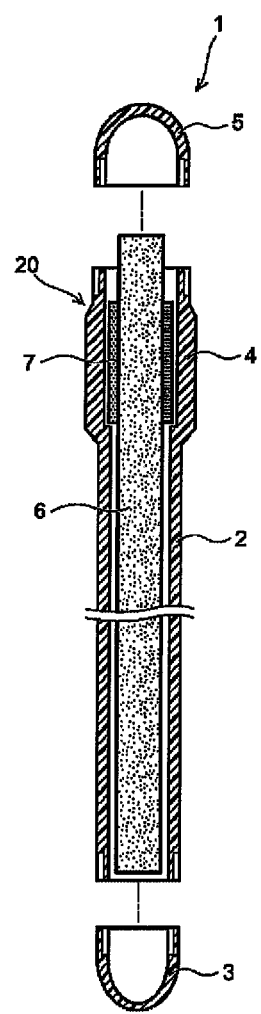
FIG. 2A is an explode cross-section view illustrating an example of the soil moisture indicator.
Figure 2B:
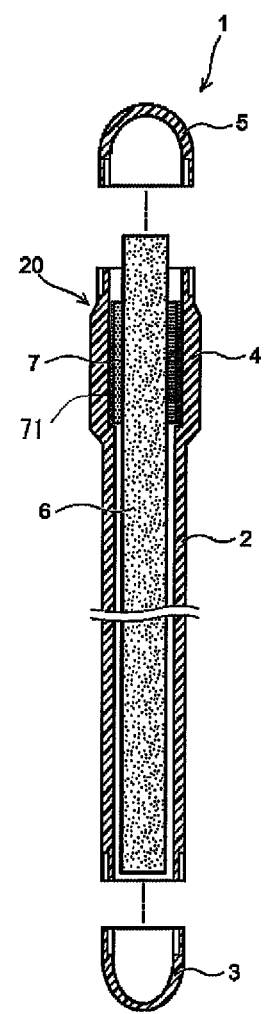
FIG. 2B is an exploded cross-section view illustrating an alternative example of the soil moisture indicator.

Aspects of the soil moisture indicator FIGS. 1A, 1B are views illustrating an example of the soil moisture indicator. FIG. 1A is a front view illustrating an example of the soil moisture indicator 1, and FIG. 1B is a side view illustrating an example of the soil moisture indicator 1. FIGS. 2A, 2B are the exploded cross-section views illustrating the example of the soil moisture indicator. As illustrated in such FIGs, the soil moisture indicator 1 comprises a main body unit 2, an apical end 3, a display 4, a top end portion 5, a water-absorbing material 6 and a color changeable unit 7.

The main body unit 2 is hollow (e.g., cylinder) and made of a material blocking water (no water penetrates). The main body unit 2 can be made of specifically any material such as plastic such as polycarbonate and ABS resin and a metal, which water does not pass thorough, but such as materials not deteriorated by water and microorganisms in the soil is preferable and, from such a standpoint, polycarbonate is further preferable.

The apical end 3 is connected to one end of the main body unit 2 in the longitudinal direction, and the display 4 is connected to the other end thereof. The water absorption opening 21 is in place in the proximity of the one end to which the apical end 3 of the main body unit 2 is connected. According to the aspect of the Embodiment of the present invention, two of each water absorption opening 21 are in place in both sides of the proximity of the end to which the apical end 3 of the main body unit 2 is connected, wherein the opening has a predetermined length (e.g., approximately 2 cm to 5 cm) and a predetermined width (e.g., approximately 1 mm to 3 mm). The water-absorbing material 6, which is inserted into the inside of the main body unit 2, is exposed through the water absorption opening 21. In addition, the shape, size and number of the water absorption opening 21 is not limited to the above, and can be arbitrarily designed in the scope, as long as it is well capable of absorbing water from the soil and securing the strength of the main body unit 2.

The color of the main body unit 2 is preferably opaque and discreet such as white, beige and black, and less bright. In addition, the color is preferably capable of enhancing the color of the color changeable unit 7 to be brilliant (easily recognized), i.e., a complimentary color or an opposite color to each other.

The evaporation opening 22 is in place in the proximity of the one end to which the display 4 of the main body unit 2 is connected. According to the aspect of the Embodiment of the present invention, two of each evaporation opening 22 are in place in both sides of the proximity of the end to which the display 4 of the main body unit 2 is connected, wherein the opening has a predetermined length (e.g., approximately 5 mm to 15 mm) and a predetermined width (e.g., approximately 1 mm to 3 mm). The evaporation opening 22 is an opening allowing water, which is in the soil and absorbed by the water-absorbing material 6, to evaporate and discharge into the air. In addition, the shape, size and number of the evaporation opening 22 are not limited to the above, and can be arbitrarily designed in the scope, in which the drying rate of the water-absorbing material and pF value causing a color tone change of the color changeable unit 7 are adequate.

The end portion, to which the display 4 of the main body unit 2 is connected, is formed to have, for example, an oval shape corresponding to the cross-section shape of the display 4. The cross-section of the other portions of the main body unit 2 is circular, so that the closer to the end, the broader the width viewing from the front is, and as a result, the cross-section is figured so as to be oval along with changing. In addition, the guideline 23 that can provide a target of the depth in the soil to be inserted is given in the side of the main body unit 2. The guideline 23 is given in the position which is approximately 1 cm far from the water evaporating opening 21 in the direction toward the end where the evaporation opening 22 is set up, and the soil moisture indicator 1 is inserted so that the guideline 23 roughly coincides with the surface line of the soil and then used in such a state.

The total length of the main body unit 2 is preferable in the range of 5 to 40 cm so that the display 4 can be exposed from the container such as a planter. In addition, the outer diameter thereof is preferably approximately in the range of 5 to 10 mm at facilitating insertion thereof into the soil and the inner diameter thereof is preferably approximately in the range of 4 to 8 mm so as to provide enough strength.

The main body unit 2 can be manufactured by any method that can provide such an above structure at the bottom line, e.g., using an injection molding. In addition, the tubular material can be processed to manufacture, or the cylinder material can be cut in half in the longitudinal direction and the water-absorbing material 6 is filled (set up) followed by connecting each half.

As set forth above, the apical end 3 is connected to the one end of the main body unit 2 and seals the opening at the one end of the main body unit 2. The connection method between the main body unit 2 and the apical end 3 is arbitrarily decided, and for example, the one end of the main body unit 2 is pressed into the apical end 3 or screwed together. The apical end 3 is shaped as e.g., a cone, i.e., having a narrow and sharp end. When the soil moisture indicator 1 is inserted to use, the apical end 3 becomes the tip member and has a sharp shape that facilitates the smooth insertion. In addition, the one end of the main body unit 2 is sealed, so that the apical end 3 can block the soil from getting into the inside of the main body unit 2 when inserting the soil moisture indicator 1 into the soil and the contact condition between the water absorption opening 21 and the soil can be kept constant regardless how to insert.

The display 4 is a clear and hollow member and connected to the other end of the main body unit 2 as set forth above. The connection method between the main body unit 2 and the display 4 is arbitrarily decided, and for example, the display 4 is pressed into the one end of the main body unit 2 to connect each other. The display 4 is made of a clear material allowing to visually recognize the inside hollow space from anywhere around. It is preferable that the color of the display 4 is colorless, but it may be colored if the color change of the color tone of the color changeable unit 7 placed in the inside hollow space of the display 4 is recognizable. In addition, the hollow space of the display 4 is preferably to be recognized from anywhere around, but such a feature is not mandatory, and it is acceptable if a part of the hollow space can be recognized based on the partial clearness. The main housing 20 is wholly structured when the display 4 is connected to the other end of the main body unit 2.

The top end portion 5 connecting with the end of the opposite side of the main body unit 2 relative to the display 4 covers the hollow portion of the display 4 and defines the top side of the soil moisture indicator 1. The top end portion 5 is made to provide, for example, an oval shape cross-section corresponding to the cross-section shape of the display 4. In both sides of the top end portion 5, each of evaporation opening 51 (one example of the second evaporation of the present invention) is in place in each side as the opening has a predetermined length (e.g., approximately 5 mm to 15 mm) and a predetermined width (e.g., approximately 1 mm to 3 mm). The evaporation opening 51 is an opening allowing water, which is in the soil and absorbed by the water-absorbing material 6, to evaporate and discharge into the air as well as the evaporation opening 22 placed in the main body unit 2. In addition, the shape, size and number of the evaporation opening 51 are not limited to the above, and can be arbitrarily designed in the scope, in which the drying rate of the water-absorbing material 6 and pF value causing a color tone change in the color changeable unit 7 are adequate. In addition, only one of evaporation opening 22 and evaporation opening 51 can be equipped from a design standpoint.

The water-absorbing material 6 fills the respective insides of the main body unit 2, the display 4, and the inside hollow space of the top end portion 5 and at least the range from the water absorption opening 21 to the evaporation opening 51 of the top end portion 5. In addition, in the aspect in which the top end portion 5 has no evaporation opening 51, it is acceptable that the water-absorbing material 6 may just fill at least from the water absorption opening 21 to the display 4. The water-absorbing material 6 absorbs up water in the soil from the water absorption opening 21 to the display 4 against the gravity utilizing the capillary phenomenon. It is preferable that the water-absorbing material 6 is made of a fine fabric to provide an enough capillary action. In addition, it is preferable that an oil component of the material for the water-absorbing material 6 is satisfactorily removed. For example, the water-absorbing material 6 can be a cotton cloth rod from which the oil component is removed by processing refined-bleaching.

The color changeable unit 7 is a sheet material containing a hydrochromic ink of which color tone varies depending on the water absorbed state (wet state) and the dry state. The color changeable unit 7 covers the entire circumference of the water-absorbing material 6 at the position where is visually recognizable from the outside thereof through the display 4 and is in place as appressed to the water-absorbing material 6. According to such an arrangement, the color changeable unit 7 displays a different color tone between the time when the water-absorbing material 6 is absorbing water contained enough in the soil and the time when the water-absorbing material 6 is dried along with the dried soil. Such a color tone change takes place around the entire circumference of the water-absorbing material 6. It is preferable that the hydrochromic ink included in the color changeable unit 7 changes the color tone per se clearly depending on respectively the wet state and the dry state, e.g., white when dried and blue when wet. The color tone change can be observed through the display 4. Now, FIG. 2B is the exploded cross-section view illustrating an alternative example of the soil moisture indicator. Referring to FIG. 2B, the color changeable unit 7 can be housed inside the clear cylinder 71 having an inner diameter thereof larger than the outer diameter of the water-absorbing material 6. According to such a structure, the cylinder shape thereof is easily (steadily) kept while facilitating a handling when manufacturing.

A sheet material applicable to the color changeable unit 7 is e.g., papers and cloths, but it is preferable that the material is less capable of holding water than the water-absorbing material 6 so that the color changeable unit 7 cannot hold water when the water-absorbing material 6 is dried and has enough durability. In addition, it is preferable that the color changeable unit 7 is made of the material to which the hydrochromic ink is readily adhered. When cotton, from which an oil is removed, is applied to the water-absorbing material 6, for example, such as a woven cloth as the sheet material to make the color changeable unit 7, a cotton cloth having more remained cotton wax than the water-absorbing material 6 and T/C velor (velor is cloth made of blended yarn of cotton and polyester) can be desirably used.

A pF value indicating the change of the color tone relative to the soil moisture indicator 1 can be adjusted using a variety of parameters. For example, a drying rate of the water-absorbing material 6 is adjustable in accordance with the cross-section area of the evaporation opening 22 and 51 and the shape thereof, so that the pF value causing the color tone change of the color changeable unit 7 can be adjusted. Specifically, the larger the cross-section area of the evaporation opening 22 is designed, the faster the water-absorbing material 6 dries, so that the pF value, indicating the color tone change, can be adjusted to be small (i.e., so that a reaction would not take place unless the water content of the soil is large). In addition, the pF value indicating the color tone change can be adjusted based on such as the length of the main body unit 2 (particularly, the length from the water absorption opening 21 to the display 4), the diameter thereof, the cross-section area of the water absorption opening 21, the material of the water-absorbing material 6, the density of the water-absorbing material 6 and the twisting level.

The soil moisture indicator 1, having such an above aspect, is used by inserting the one end thereof, at which the water absorption opening 21 is in place, into the soil. Under such a condition in use, the water-absorbing material 6 exposed from the water absorption opening 21 tends to absorb up the water in the soil utilizing the capillary action (phenomenon). The water-absorbing material 6 is wetted until around the display 4 when the pF value is low due to the enough water in the soil. The color changeable unit 7 covering the display 4 reacts and provides the color tone indicating the water-absorbed state. Whereas, the water-absorbing material 6 around the display 4 is in the dried state when the pF value is high due to not-enough amount of water in the soil, so that the color changeable unit 7 covering the display 4 provides the color tone indicating the dried state. The color tone changes when the soil becomes dried, so that the soil moisture indicator 1 can display the dryness of the soil to the user. Such a soil moisture indicator 1 transits between the wet state and the dried state corresponding to the watering and the dryness of the soil and can be used repeatedly multiple times.

(Structure of Water Detection Unit)

Figure 3:
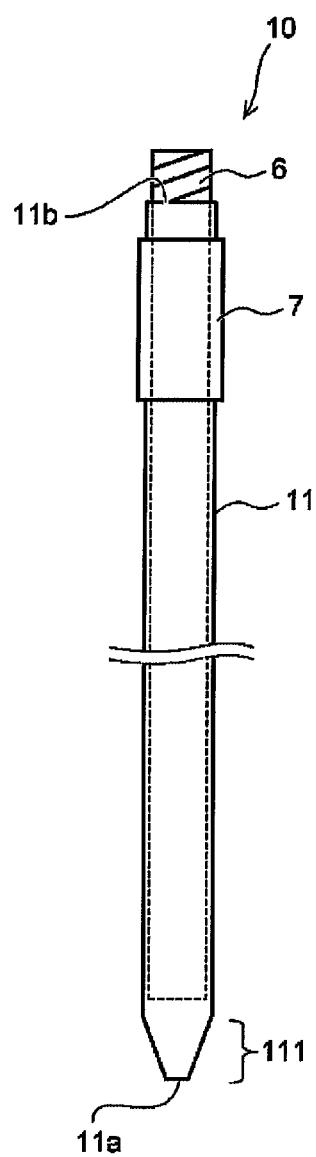
FIG. 3 is a schematic front view illustrating the structure of the water detection unit according to the aspect of the Embodiment of the present invention.

FIG. 3 is a schematic front view illustrating the structure of the water detection unit according to the aspect of the Embodiment of the present invention. The water detection unit 10, according to the aspect of the present Embodiment, is applied to the soil moisture indicator 1 as set forth above. The water detection unit 10 comprises a cylinder housing 11, a water-absorbing material 6 and a color changeable unit 7. The cylinder housing 11, e.g., a cylinder made of a resin, has a hollow structure. In addition, the cylinder housing 11 can be a soft film (flexible plastic) or made of a gum or a paper. The apical portion 111 from the one end 11a of the cylinder housing 11 to the predetermined position has a reduced diameter. The other end 11b side far from the apical portion 111 of the cylinder housing 11 has an almost constant inner diameter and the almost constant outer diameter.

The water-absorbing material 6 is housed inside the cylinder of the cylinder housing 11. The water-absorbing material 6 is housed in the side of the other end 11b from the apical portion 111 of the cylinder housing 11. The water-absorbing material 6, e.g., the twisted cotton cloth, from which the oil component is removed by processing refined-bleaching, is housed in the cylinder of the cylinder housing 11. The water-absorbing material 6 projects slightly from the other end 11b of the cylinder housing 11 while housed in the cylinder housing 11.

The color changeable unit 7 is mounted to the outer circumference of the cylinder case 11. The color changeable unit 7 is a cylinder made of the sheet material containing the hydrochromic ink and connected to the outer circumference of the cylinder housing 11 at the predetermined position. Accordingly, a contact between the water-absorbing material 6 and the color changeable unit 7 is specified by the cylinder housing 11. The color changeable unit 7 can be a cylinder per se, but also can be better provided the sheet containing the hydrochromic ink is adhered to the inner wall of the clear cylinder having the larger inner diameter than the outer diameter of the cylinder housing 11. According to such a structure, the cylinder shape thereof is easily (steadily) kept while facilitating a handling when manufacturing.

Such a water detection unit 10 has a rod-shaped structure, wherein the water-absorbing material 6 and the color change unit 7 are being supported as the cylinder housing 11 functioning as the supporting member. The water detection unit 10 can be provided, as a replacement member (i.e., refill) separately from the finish product of the soil moisture indicator 1. According to the rod-shaped water detection unit 10 having the water-absorbing material 6 and the color changeable unit 7, the water-absorbing material 6 and the color changeable unit 7 applied to the soil moisture indicator 1 can be readily exchangeable. Given the water-absorbing material 6 and the color change unit 7 are exchangeable as the water detection unit 10, the water-absorbing material 6 and the color changeable unit 7 capable of making a judgment for the best pF corresponding to each plant when the water-absorbing material 6 is deteriorated. In addition, the water-absorbing material 6 is housed in the cylinder of the cylinder housing 11, so that the water-absorbing material won't swell even when the water detection unit 10 is not being used for a long time and can be easily mounted to the soil moisture indicator 1.

(Manufacturing Method for the Water Detection Unit)

FIG. 4A, FIG. 4B, FIG. 5A, FIG. 5B, FIG. 6A, FIG. 6B are schematic views illustrating the manufacturing method for the water detection unit. First, referring to FIG. 4A, the cylinder housing 11 is prepared. The cylinder housing 11 has an almost constant inner diameter and the almost constant outer diameter from the one end 11a to the other end 11b.

Figure 4A:
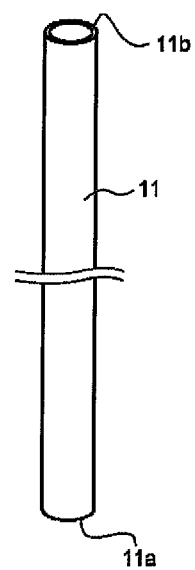
FIG. 4A is a schematic view illustrating the manufacturing method for the water detection unit according to the aspect of the Embodiment of the present invention.
Figure 4B:
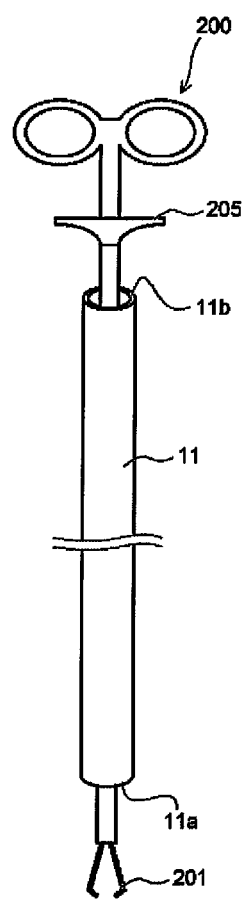
FIG. 4B is a schematic view illustrating the manufacturing method for the water detection unit according to the aspect of the Embodiment of the present invention.

Next, referring to FIG. 4B, a pickup tool (retractable reaching tool) 200 is inserted into the inside of the cylinder from the other end 11b of the cylinder housing 11. Then, the tip grabber 201 of the pickup tool 200 projects from the one end 11a of the cylinder housing 11. The grabber 201 of the pickup tool 200 is retractable (openable and closable) by operating the lever 205.

Figure 5A:
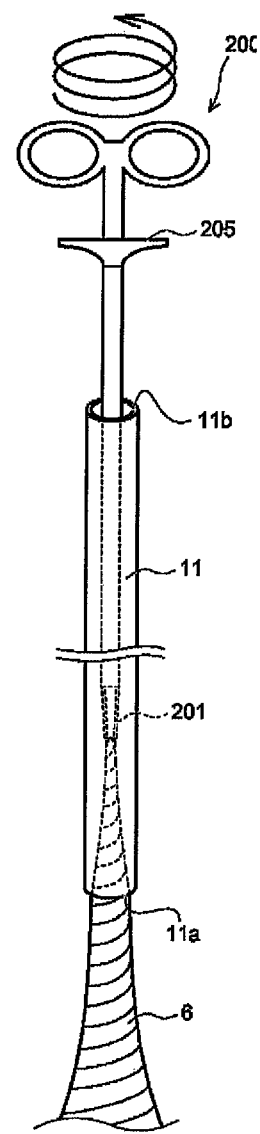
FIG. 5A is a schematic view illustrating the manufacturing method for the water detection unit according to the aspect of the Embodiment of the present invention.

Next, referring to FIG. 5A, the end of the water-absorbing material 6 is grasped with the grabber 201 by operating the lever 205 of the pickup tool 200. Then, the pickup tool 200 is pulled while being rotated in such a state. Therefore, the water-absorbing material 6 is pulled into the inside of the cylinder of the cylinder housing 11 while being twisted. The rotation number and the retrieving rate of the pickup tool 200 are adjustable, so that the water absorbability can be varied by changing the twisting level of the water-absorbing material 6 inside the cylinder housing 11.

Figure 5B:
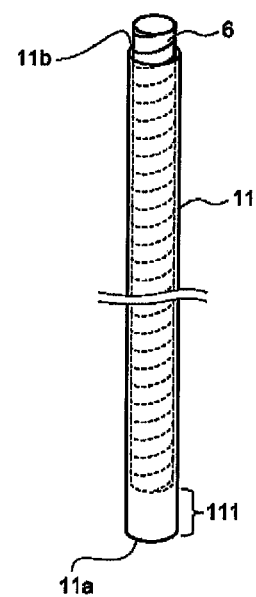
FIG. 5B is a schematic view illustrating the manufacturing method for the water detection unit according to the aspect of the Embodiment of the present invention.

Next, referring to FIG. 5B, the pickup tool 200 is removed while the water-absorbing material 6 is still being pulled inside the cylinder housing 11. At this time, no water-absorbing material 6 must be remained in the apical portion 111 of the cylinder housing 11. In addition, the water-absorbing material 6 projects slightly from the other end 11b of the cylinder housing 11.

Figure 6A:
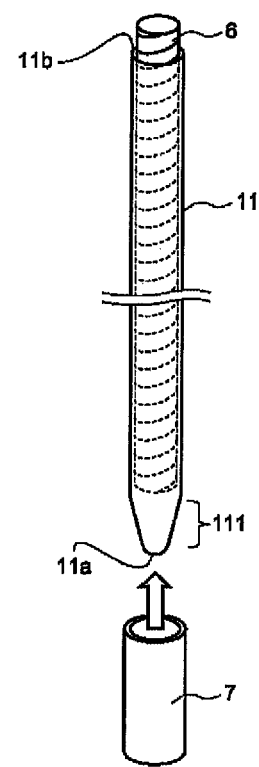
FIG. 6A is a schematic view illustrating the manufacturing method for the water detection unit according to the aspect of the Embodiment of the present invention.

Next, referring to FIG. 6A, the diameter of the apical portion 111 of the cylinder housing 11 is reduced. For example, the cylinder housing 11 is first made of a heat shrinkable material. Then, the apical portion 111 is shrunk by adding predetermined heat amount. Once the diameter of the apical portion 111 is shrunk, the water-absorbing material 6 cannot be pulled out from the one end 11a of the cylinder housing 11.

Next, the color changeable unit 7 is inserted from the apical portion 111 of the cylinder housing 11. The color changeable unit 7 is formed as a cylinder in advance. Next, such a cylinder color changeable unit 7 is inserted from the apical portion 111 of the cylinder housing 11. The diameter of the apical portion 111 is reduced, so that the cylinder color changeable unit 7 can be easily inserted.

Figure 6B:
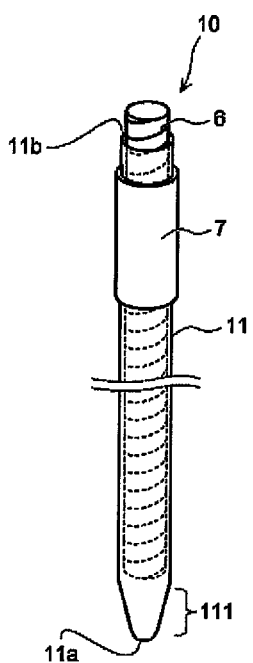
FIG. 6B is a schematic view illustrating the manufacturing method for the water detection unit according to the aspect of the Embodiment of the present invention.

And referring to FIG. 6B, the color changeable unit 7 is inserted near by the other end 11b of the cylinder housing 11 and then, the manufacturing of the water is complete. The inner diameter of the cylinder color changeable unit 7 is the same as the outer diameter of the cylinder housing 11. Accordingly, the color changeable unit 7 can be connected along the outer circumference 11. In addition, the color changeable unit 7 is preferably connected to the outer circumference 11 at the slidable level (tightness). Such a level facilitates to pull out only the cylinder housing 11 when the water detection unit 10 is applied.

(Main Body Housing Structure)

Figure 7:
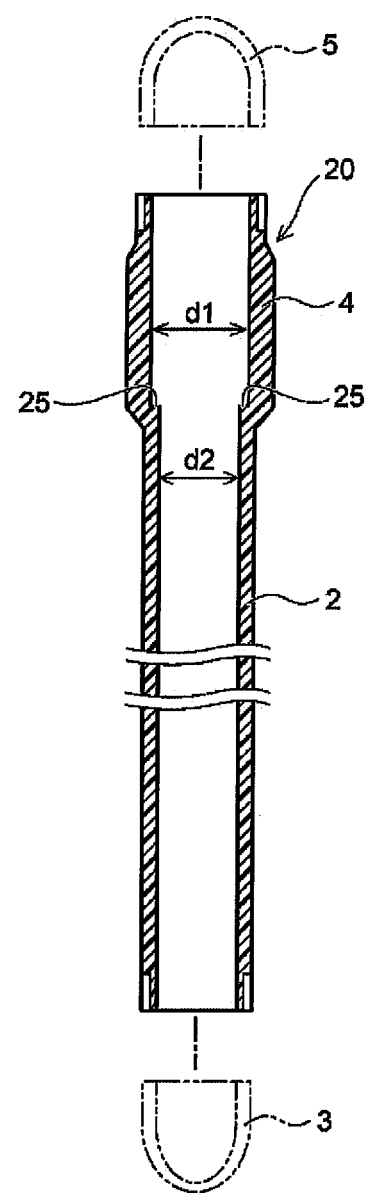
FIG. 7 is a schematic cross-section view illustrating the structure of the main body housing according to the aspect of the Embodiment of the present invention.

FIG. 7 is a cross-section view illustrating the structure of the main body housing according to the aspect of the present Embodiment. The main body housing 20, according to the aspect of the present Embodiment, is applied to the soil moisture indicator 1 as set forth above. The main body housing 20 is in place as capable of housing the water detection unit 10. The main body housing 20 comprises the main body unit 2 and the display 4 connected to the other end of the main body unit 2. The main body housing 20 is a cylinder and has the approximately oval hollow space viewing from the longitudinal direction relative to the main body unit 2 and display 4. The end portion of the main body unit 2 has a screw and a connection member to mount the tip portion 3 and the end portion of the display 4 has a screw and a connection member to mount the end portion 5.

According to the main body housing 20 in such a way, the inner diameter d1 of the display 4 is larger than the inner diameter d2 of the main body unit 2. Specifically, the inner diameter d2 of the main body unit 2 is larger than the outer diameter of the cylinder housing 11 relative to the water detection unit 10 and smaller than the outer diameter of the color changeable unit 7. In addition, the inner diameter d1 of the display 4 is larger than the outer diameter of the color changeable unit 7 relative to the water detection unit 10. The inner diameter d1 of the display 4 is larger than the inner diameter d2 of the main body unit 2, so that an uneven element (like a step) 25 can be set up between the main body unit 2 and display 4 relative to the inner wall of the main body housing 20.

The inner diameter of the main body housing 20 is larger than the outer diameter of the cylinder housing 11 of the water detection unit 10, so that the water detection unit 10 as the whole cylinder housing 11 can be inserted into the inside of the main body housing 20. In addition, according to the above aspect, the inner diameter d1 and d2 are set up, relative to the mounting method for the water-absorbing material 6 and the color changeable unit 7 as set forth later, so that the cylinder housing 11 can be pulled out from the main body housing 20 while leaving the water-absorbing material 6 and the color changeable unit 7 to the predetermined position after the water detection unit 10 is housed in the main body housing 20.

(Mounting Method for the Water-Absorbing Material and the Color Changeable Unit Based on the Water Detection Unit)

FIG. 8A, FIG. 8B, FIG. 9A, FIG. 9B are schematic views illustrating examples of the mounting method for the water-absorbing material and the color changeable unit based on the water detection unit. In addition, for convenience of explanation, only the main body unit 2 is illustrated to show the cross-section in FIG. 8A. First, referring to FIG. 8A, the empty main body housing 20 or the main body housing 20 without the water-absorbing material 6 and the color changeable unit 7, which are pulled out, is prepared. Next, the water detection unit 10 is inserted into the inside of the main body housing 20 from the display 4 side. The diameter of the apical portion 111 of the cylinder housing 11 is reduced, so that the water detection unit 10 can be inserted into the inside of the cylinder of the main body housing 20 from the apical portion 111.

Figure 8A:
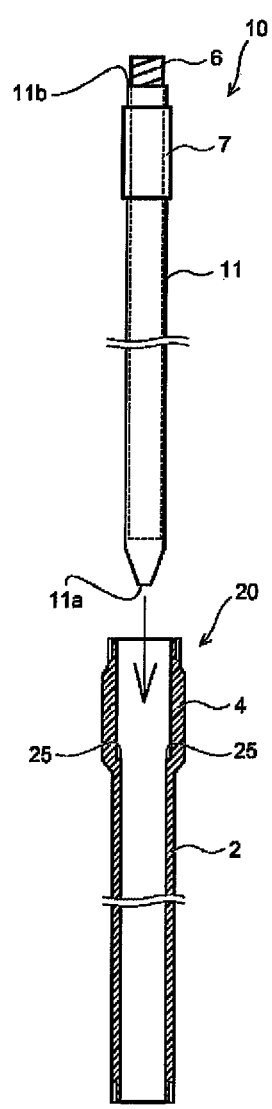
FIG. 8A is a schematic view illustrating a mounting method for the water-absorbing material and the color changeable unit based on the water detection unit according to the aspect of the Embodiment of the present invention.
Figure 8B:
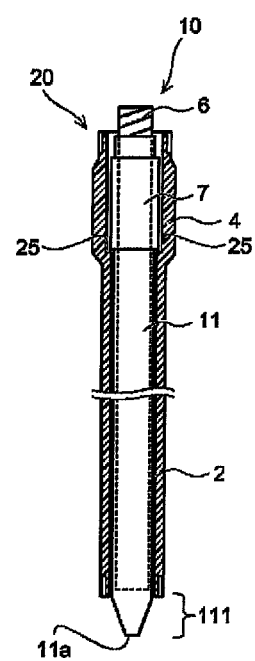
FIG. 8B is a schematic view illustrating the mounting method for the water-absorbing material and the color changeable unit based on the water detection unit according to the aspect of the Embodiment of the present invention.

Referring to FIG. 8B, the apical portion 111 of the cylinder housing 11 projects to be exposed from the tip of the main body unit 2 when the water detection unit 10 is inserted into the main body housing 20. In addition, the end of the water-absorbing material 6 of the water detection unit 10 projects to be exposed from the end of the display 4 side of the main body housing 20. In addition, the color changeable unit 7 is in place at the position of the display 4.

Figure 9A:
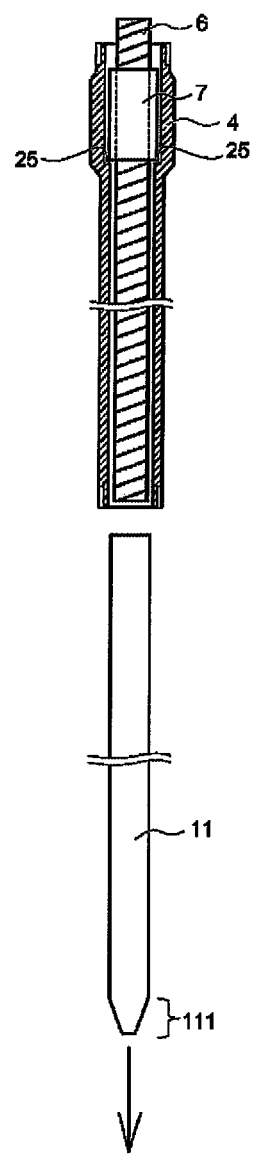
FIG. 9A is a schematic view illustrating the mounting method for the water-absorbing material and the color changeable unit based on the water detection unit according to the aspect of the Embodiment of the present invention.

Next, referring to FIG. 9A, the cylinder housing 11 projected from the apical end of the main body unit 2 of the main body housing 20 is pulled and the cylinder housing 11 is pulled out from the main body housing 20. At this time, the cylinder housing 11 is pulled while the water-absorbing material 6 projected (exposed) from the display 4 side of the main body housing 20 is being held. Accordingly, the cylinder housing 11 alone can be pulled out while leaving the water-absorbing material 6 in the main body housing 20.

Figure 9B:
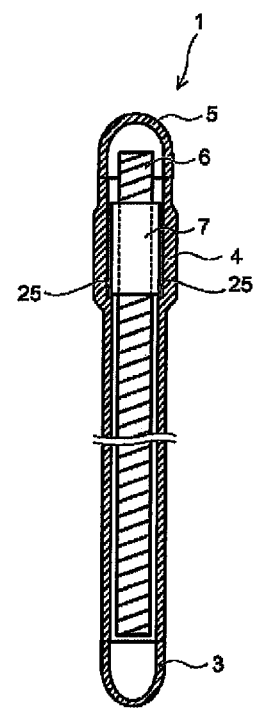
FIG. 9B is a schematic view illustrating the mounting method for the water-absorbing material and the color changeable unit based on the water detection unit according to the aspect of the Embodiment of the present invention.

In addition, when the cylinder housing 11 is pulled off, the movement of the color changeable unit 7 is restricted, and in more detail, the color changeable unit 7 gets stuck at the uneven element 25 in the inner wall of the main body housing 20, so that the cylinder housing 11 is pulled off while leaving behind the color changeable unit 7 at the position of the display 4. The movement of the clear cylinder 71 is also restricted when the clear cylinder 71 is equipped. Specifically, the color changeable unit 7 and the clear cylinder 71 get stuck at the uneven element 25 in the inner wall of the main body housing 20, so that the cylinder housing 11 is pulled off while leaving behind the color changeable unit 7 at the position of the display 4. Referring to FIG. 9B, the apical end 3 is mounted to the end of the tip of the main body housing 20 and the top end portion 5 is mounted to the end of the display 4 following pulling off the cylinder housing 11. Accordingly, the manufacturing of the soil moisture indicator 1 comprising the water-absorbing material 6 and the color changeable unit 7 at the predetermined position of the main body housing 20 is complete.

In addition, when the water-absorbing material 6 and the color changeable unit 7 are pulled out from the main body housing 20, the top end portion 5 is taken off and then the exposed (projected) water-absorbing material 6 can be pulled out. Accordingly, the color changeable unit 7 can be pulled out from the main body housing 20 along with the water-absorbing material 6. The new water detection unit 10 can be inserted into the empty main body housing 20 when needed.

(Alternative Embodiment)

Figure 10:
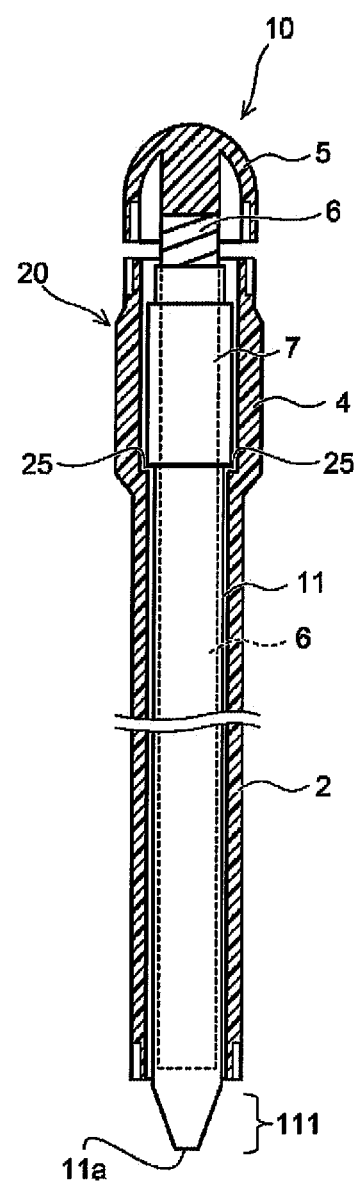
FIG. 10 is a schematic view illustrating an alternative Embodiment 1 of the present invention.

FIG. 10 is a schematic view illustrating an alternative Embodiment 1 of the present invention. Referring to FIG. 10, the top end portion 5 is mounted to the end of the water-absorbing material 6 projected from the cylinder housing 11 of the water detection unit 10. When such a water detection unit 10 is inserted into the main body housing 20, the top end portion 5 is fixed to the end of the main body housing 20 following inserting the cylinder housing 11 of the water detection unit 10 into the main body housing 20. After the cylinder housing 11 projected from the apical end 3 of the main body unit 2 is pulled and pulled off from the main body housing 20. At this time, the water-absorbing material 6 is held in the main body housing 20 together with the top end portion 5, so that the end of the water-absorbing material 6 is not needed to be held and the cylinder housing 11 alone can be easily pulled out.

Figure 11:
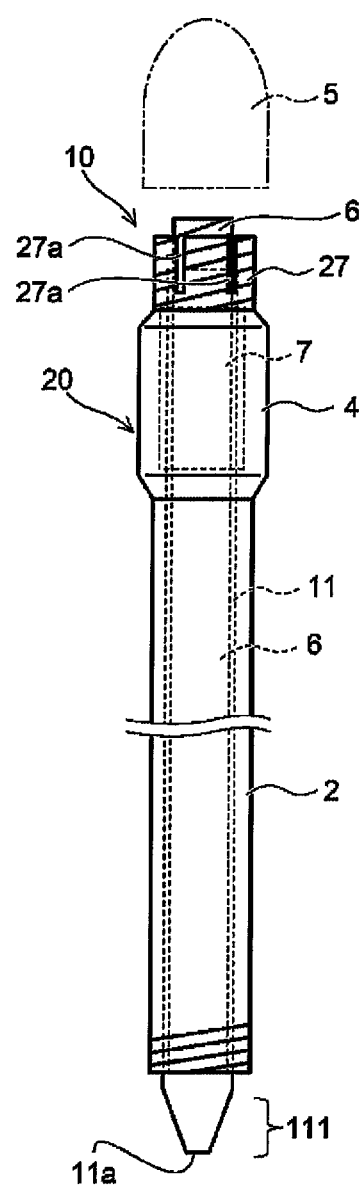
FIG. 11 is a schematic view illustrating an alternative Embodiment 2 of the present invention.

FIG. 11 is a schematic view illustrating an alternative Embodiment 2 of the present invention. Referring to FIG. 11, a slit 27a is in place at the screw member 27 to mount the top end 5 to the end of the display 4 side of the main body housing 20. Accordingly, the top end portion 5 is fastened with the screw member 27, so that the slip 27a is gradually narrow and the inner diameter of the screw member 27 is smaller.

According to such a main body housing 20, the water detection unit 10 is inserted into the main body housing 20 followed by fastening the top end portion 5 to the screw 27, so that the end portion of the water-absorbing material 6 can be fastened and connected to the inner side of the screw 27 utilizing the diameter reduction of the screw 27. Given the top end portion 5 is fastened and the end of the water-absorbing material 6 is fixed, the end of the water detection unit 10 is not needed to be held and the cylinder housing 11 alone can be easily pulled out when the main body housing 11 projected from the top of the main body unit 2 is pulled off from the main body housing 20.

(Alternative Embodiment of the Water Detection Unit)

Figure 12A:
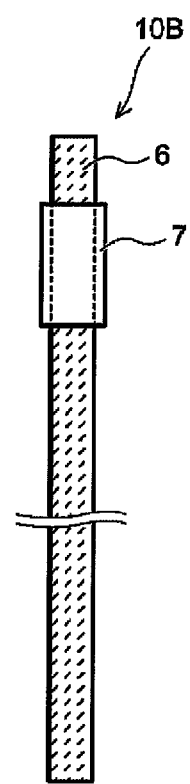
FIG. 12A is a schematic front view illustrating the structure of the other water detection unit according to the aspect of the Embodiment of the present invention.

FIG. 12A is a schematic front view illustrating the alternative embodiment of the water detection unit. Referring to FIG. 12A, the water detection unit 10B is applied to the soil moisture indicator 1 set forth above. The water detection unit 10B comprises a rod water-absorbing material 6 and a color changeable unit 7 mounted to the outer circumference of the water-absorbing material 6. Specifically, the water detection unit 10B, referring to FIG. 12A, has no cylinder housing 11 in FIG. 3. The water detection unit 10B can be provided, as a replacement member (i.e., refill) separately from the finish product of the soil moisture indicator 1 as well as the water detection unit 10.

Figure 12B:
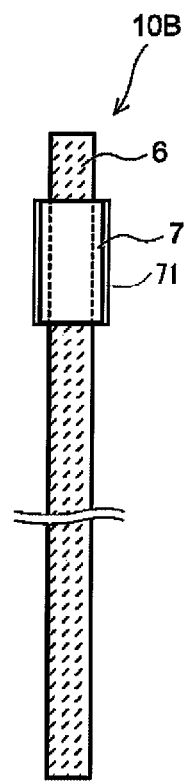
FIG. 12B is a schematic front view illustrating the structure of the other water detection unit according to the aspect of the alternative Embodiment of the present invention.

The water-absorbing material 6 of the water detection unit 10B, referring to FIG. 12A, has formability to form a rod per se and the (horizontal) size is formed to be narrower than the inner diameter d2 of the main body unit 2 of the main body housing 20 when not in use. According to such a structure, the water detection unit 10B can be easily exchanged. In addition, it is preferable that the water-absorbing material 6 swells and provides a larger diameter when absorbing water. According to such a way, the color changeable unit assuredly varies the color thereof by adhering the color changeable unit 7 to the water-absorbing material 6 when in use while ensuring easy-exchangeability therefor. In addition, it is preferable that the color tone change of the water detection unit 10B takes place quickly (desirably around in a few minutes to ten-and-several minutes) corresponds to the water content in the soil. Now, FIG. 12B is a schematic front view illustrating the structure of the other water detection unit according to the aspect of the alternative Embodiment of the present invention. Referring to FIG. 12B, the water detection unit 10B has a larger inner diameter than the outer diameter of the water-absorbing material 6 and can comprise the clear cylinder 71 having the color changeable unit 7 thereinside. According to such a structure, the cylinder shape thereof is easily (steadily) kept while facilitating a handling when manufacturing.

An unwoven cloth, a sliver, a chemical fiber can be applied to the water-absorbing material 6 to preserve (guarantee) such properties.

When the unwoven cloth is applied to the water-absorbing material 6, the water absorbability can be freely designed depending on the density of the unwoven cloth. For example, given the density of the unwoven cloth is low, the water detection unit 10B that changes the color tone thereof at the low PF value can be designed. Whereas, given the density of the unwoven cloth is high, the water detection unit 10B that changes the color tone thereof at the high pF value can be designed.

When the unwoven cloth is applied to the water-absorbing material 6, the shape retaining agent can be applied or added by immersing, and so forth to provide the shaped water-absorbing material 6 with maintaining the shape. Such a shape retaining agent includes such as a starch, carboxyl methyl cellulose and the mixture thereof.

A polymer having high-water absorbability can be adhered to the unwoven cloth as the water-absorbing material 6. The polymer having a high-water absorbability coats the unwoven cloth. The water-absorbing material 6 is made by making a rod of the unwoven cloth coated with the polymer having high-water absorbability and pressing to shape. At this time, a binder can be added to maintain the adhesion state of the polymer having high-water absorbability. The polymer having high-water absorbability is adhered to the unwoven cloth, so that the water detection unit 10B that changes the color tone thereof at the high pF value compared to not adhered unwoven cloth can be designed. Specifically, the color of the color changeable unit 7 varies even when the soil is more dried. In addition, the polymer having high-water absorbability can be applied to the water-absorbing material 6 that is applied to the water detection unit 10 according to the aspect of the Embodiment set forth above.

In addition, the water-absorbing material 6 can include a preservative. A variety of bacteria is present in the soil, so that the water-absorbing material 6 may be contaminated with the bacteria coming therein with absorbed water from the soil. Given such a preservative is included in the water-absorbing material 6, a corrosion of the water detection unit 10B can be prevented. In addition, the preservative is contained in the water-absorbing material 6, it is preferable that the binder can maintain the adhesion state relative to the preservative. In addition, the preservative can be applied to the water-absorbing material 6 that is applied to the water detection unit 10 according to the aspect of the Embodiment set forth above.

In addition, the binder included for maintaining the adhesion state of the polymer having high-water absorbability and the preservative may function to improve the property for maintaining the shape.

Figure 13A:
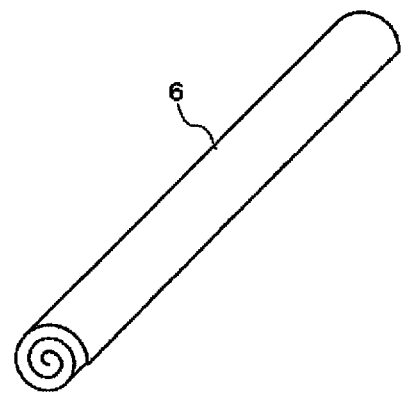
FIG. 13A is a schematic diagram illustrating the manufacturing method for the other water detection unit according to the aspect of the Embodiment of the present invention.
Figure 13B:
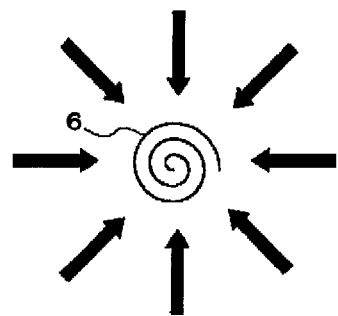
FIG. 13B is a schematic diagram illustrating the manufacturing method for the other water detection unit according to the aspect of the Embodiment of the present invention.
Figure 14:
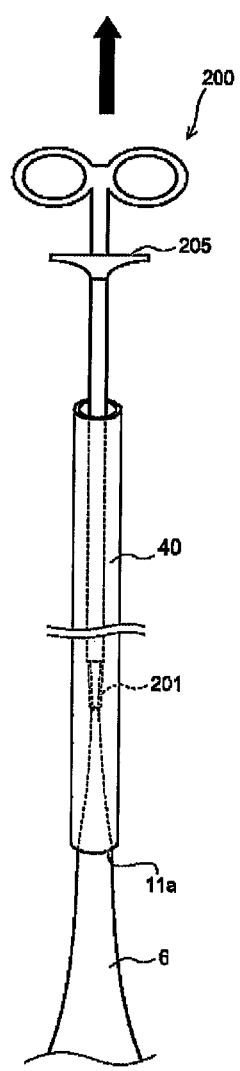
FIG. 14 is a schematic diagram illustrating the manufacturing method for the other water detection unit according to the aspect of the Embodiment of the present invention.

Referring to FIG. 13A, FIG. 13B, for example, when the unwoven cloth is applied to the water-absorbing material 6, the unwoven cloth is wound to make a rolled-rod (referring to FIG. 13A) and pressed further to make a desired shape for shaping the water-absorbing material 6 to be the rod having the desired outer diameter. Otherwise, referring to FIG. 14, the unwoven cloth can be inserted into the cylinder 30, having a predetermined diameter, to pass therethrough and then, the unwoven cloth can be pulled up using the pickup tool 200 while being wrinkled up to provide the water-absorbing rod material 6 having the desired diameter. The inner diameter of the cylinder (tube), through which the unwoven cloth passes, can be determined based on the desired outer shape that the water-absorbing material should have after shaped. The unwoven cloth pulled out, according to the above aspect, can be subject to a compression molding if needed. The shaping method, referring to FIG. 13A, FIG. 13B, FIG. 14, is desired to make the unwoven cloth having a low water absorbability and preferably applied to make the water detection unit 10B of which color tone changes depending on the low pF value. According to such shaping methods, the density of the water-absorbing material 6 is low, so that the shape retaining agent just slightly affects the water absorbability when the shaping retaining agent is added. Accordingly, the shape retaining property can be improved by adding the shape retaining agent in the range in which the shape retaining agent affects the water absorbability low enough.

Further, as the alternative method as well as referring to FIG. 14, the unwoven cloth is made as a string by passing through the tube having a predetermined diameter and the obtained string unwoven cloth can be twisted to provide the rod with a predetermined outer diameter. Such a shaping method is desired to make the unwoven cloth water-absorbing material 6 having a high-density and a high-water absorbability and preferably applied to make the water detection unit 10B of which color tone changes depending on the high pF value. According to such a shaping method, the density of the water-absorbing material 6 is high, so that the shape retaining agent may badly affect the water absorbability when the shaping retaining agent is added and the quick color tone change can be damaged. Accordingly, the shape retaining agent is preferably not used. In addition, the binder may function as well as the shape retaining agent, so that it is preferable that the polymer having high-water absorbability and the preservative can be preferably used with the binder when adhered to the unwoven cloth.

In addition, it is desired that the shape retaining agent is added to the sliver to give capability of keeping the shape when the sliver, which the cotton fibers are arrayed approximately in one direction, is applied to the water-absorbing material 6. If needed, the sliver can be compressed and molded so that the desired outer diameter and the cotton density can be provided.

In addition, when the chemical fibers are applied to the water-absorbing material 6, the outer circumference of the water-absorbing material 6 made of the chemical fiber can be harder than the inner circumference of the water-absorbing material made of the chemical fiber. For example, the outer circumference of the water-absorbing material 6 made of the chemical fibers bundled to an approximate column-shape is heated to cure. Accordingly, the water-absorbing material 6 made of the chemical fibers is kept being a rod and the water absorbability thereinside can be ensured. When the chemical fibers are applied to the water-absorbing material 6, the water-absorbing material becomes more resistant against a decay due to microorganisms and bacteria, so that the durability thereof can be enhanced.

In such a way, the cylinder housing 11 is not required for the water detection unit 10B, so that the structure of the water detection unit 10B can be simplified and the production cost of the water detection unit 10B can be cut down and in addition, the water detection unit 10B having a variety of characteristic properties (e.g., water absorbability and water resistance) can be created. In addition, instead of the pickup tool 200, an apparatus for pulling out the unwoven cloth can be equipped in e.g., a factory and the rod-shaped water-absorbing material 6 made of an unwoven cloth can be made continuously. Further, the unwoven cloth is made as a string by passing through the tube having a predetermined diameter using a pulling-out apparatus and then, the obtained string unwoven cloth can be twisted to provide the rod with a predetermined outer diameter. The unwoven cloth can be shaped to provide a rod followed by cutting the rod-shaped unwoven cloth. The color changeable unit 7 is mounted to the outer circumference of the water-absorbing material 6 made of the rod-shaped cut-unwoven cloth, so that the water detection unit 10B can be manufactured. In addition, the clear cylinder 71 may enclose the color changeable unit 7 and then, the water-absorbing material 6, which is cut, can be passed through the color changeable unit 7 and the clear cylinder 71.

Figure 15:
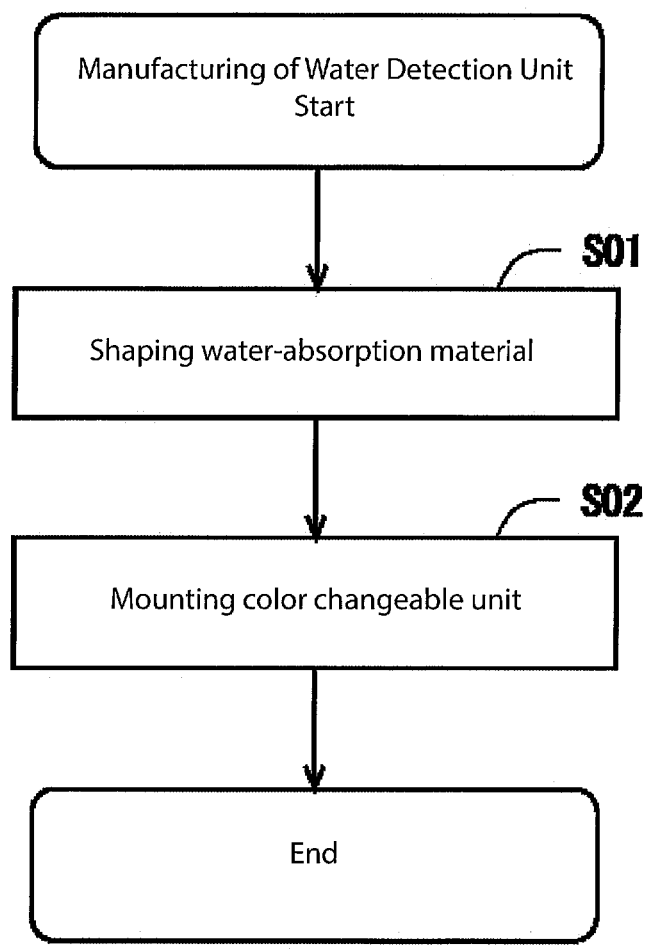
FIG. 15 is a schematic flow diagram illustrating the manufacturing method for the water detection unit according to the aspect of the Embodiment of the present invention.
Figure 16:
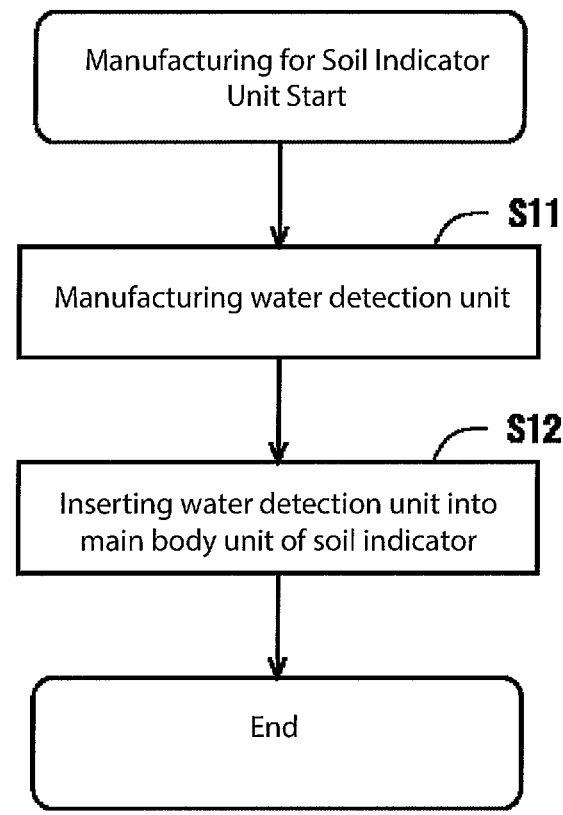
FIG. 16 is a schematic flow diagram illustrating the manufacturing method for the soil moisture indicator.

According to the aspect of the embodiment of the present invention set forth above, the manufacturing method for the water detection unit 10, 10B, of which the water-absorbing material 6 and the color changeable unit 7 can be exchanged easily, can be provided. In other words, referring to FIG. 15, the manufacturing method for the water detection unit applied to the soil moisture indicator 1, including the manufacturing method for the water detection unit 10, 10B applied to the soil moisture indicator 1, comprising steps of shaping the water-absorbing material 6 made of a rod-shaped unwoven cloth (S01); and mounting the color changeable unit 7 to the outer circumference of the water-absorbing material 6 (S02), can be provided. The water-absorbing material 6 and the color changeable unit 7 are exchangeable utilizing the water detection unit 10, 10B, so that the main body unit 2 of the soil moisture indicator 1 can be kept as is and reused by replacing the out-of-order water-absorbing material 6 and the out-of-order color changeable unit 7 with the new ones. In addition, the pF value depending on the color tone change and the water detection unit 10, 10B having specifications (such as water absorbing property and preservability) suitable for the soil can be respectively selected, so that the soil moisture indicator 1 can be easily customized in accordance with the user's preference. In addition, the manufacturing method for the water detection unit 10, 10B can be applied to the soil moisture indicator 1 in which the water detection unit 10, 10B is not subject to exchange. In addition, the manufacturing method for the soil moisture indicator can be provided by inserting the manufacture water detection unit 10, 10B into the main body unit 2 of the soil moisture indicator 1. In other words, referring to FIG. 16 of the manufacturing method for the soil moisture indicator, the manufacturing method for the soil moisture indicator 1 comprising steps of: manufacturing of the water detection unit (S11); and inserting the water detection unit 10, 10B that is manufactured at the manufacturing step (method) of the water detection unit, can be provided.

In addition, the aspect of the Embodiment and the alternative Embodiment of the present invention are set forth above, but the present invention is not limited thereto. For example, with regard to the aspect of the Embodiment and the alternative Embodiment of the present invention are set forth above, the product on which a person skilled in the art adds, deletes and changes the design arbitrarily and/or the arbitrary combination of the respective aspects of each Embodiment should be included in the scope of the present invention as long as including the aspect of the present invention.

REFERENCE OF SIGNS

1 Soil-moisture indicator
2 Main body unit
3 Apical end
4 Display
5 Top end portion
6 Water-absorbing material
7 Color changeable unit
10, 10B Water detection unit
11 Cylinder housing
11a One end
11b Other end
20 Main body housing
21 Water absorption opening
22 Evaporation opening
23 Guideline
25 Uneven element
27 Screw
27a Slit
51 Evaporation opening
111 Apical portion
200 Pickup tool
201 Grabber element
205 Lever

What is claimed is:

1. A soil moisture indicator, comprising:
a main body unit that is made of a water blocking material, has a hollow structure and further comprises a water absorbing opening in a proximity of a first end thereof in a longitudinal direction and an evaporation opening in a proximity of a second end thereof;
a display that is connected with said second end of said main body unit, of which a hollow element inside thereof is visually recognizable;
a top end portion that is freely-detachably connected with said display at an opposite end of an end connected with said main body among ends of said display and covers said hollow element of said display;
a water absorbing material that fills at least from said water absorbing opening to said display inside said main body unit and said display;
a color changeable unit that is installed as covering said water absorbing material at a position of said display and changes a color thereof depending on a state selected from a group consisting of a water-absorbing state and a dry state;
a clear cylinder that encloses said color changeable unit;
an uneven element between said main body unit and said display; and
wherein an inner diameter of said display is larger than an inner diameter of said main body unit and said uneven element restricts a movement of said color changeable unit.

2. The soil moisture indicator, according to claim 1, wherein:
said top end portion comprises a second water evaporating opening;
said water absorbing material fills respective insides of said main body unit, said display, and said top end portion from said water absorbing opening to said second water evaporating opening.

3. A main body housing, comprising:
the soil moisture indicator according to claim 1, further comprising:
said main body unit;
said display; and
an apical portion located at the first end of the main body unit.

* * * * *